United States Patent
Hausen

(10) Patent No.: US 9,138,212 B1
(45) Date of Patent: Sep. 22, 2015

(54) ANCHOR SYSTEM FOR PFO CLOSURE

(75) Inventor: Bernard A. Hausen, Redwood City, CA (US)

(73) Assignee: Cardica, Inc., Redwood City, CA (US)

( * ) Notice: Subject to any disclaimer, the term of this patent is extended or adjusted under 35 U.S.C. 154(b) by 375 days.

(21) Appl. No.: 13/186,463

(22) Filed: Jul. 19, 2011

Related U.S. Application Data

(60) Provisional application No. 61/365,729, filed on Jul. 19, 2010.

(51) Int. Cl.
*A61B 17/08* (2006.01)
*A61B 17/00* (2006.01)

(52) U.S. Cl.
CPC ... *A61B 17/0057* (2013.01); *A61B 2017/00575* (2013.01)

(58) Field of Classification Search
CPC .................................................. A61B 17/0057
USPC .................. 606/151, 213, 215–218, 200, 232
See application file for complete search history.

(56) References Cited

U.S. PATENT DOCUMENTS

| | | | | |
|---|---|---|---|---|
| 5,108,420 A * | 4/1992 | Marks | | 606/213 |
| 5,171,259 A * | 12/1992 | Inoue | | 606/213 |
| 5,246,443 A * | 9/1993 | Mai | | 606/78 |
| 5,344,439 A * | 9/1994 | Otten | | 607/126 |
| 5,474,557 A * | 12/1995 | Mai | | 606/78 |
| 5,478,354 A * | 12/1995 | Tovey et al. | | 606/219 |
| 5,674,231 A * | 10/1997 | Green et al. | | 606/142 |
| 5,695,504 A * | 12/1997 | Gifford, III et al. | | 606/153 |
| 5,853,422 A * | 12/1998 | Huebsch et al. | | 606/213 |
| 5,951,589 A * | 9/1999 | Epstein et al. | | 606/213 |
| 5,954,732 A * | 9/1999 | Hart et al. | | 606/144 |
| 6,080,183 A * | 6/2000 | Tsugita et al. | | 606/213 |
| 6,193,708 B1 * | 2/2001 | Ken et al. | | 606/1 |
| 6,193,734 B1 * | 2/2001 | Bolduc et al. | | 606/153 |
| 6,206,907 B1 * | 3/2001 | Marino et al. | | 606/215 |
| 6,231,561 B1 * | 5/2001 | Frazier et al. | | 604/500 |
| 6,306,163 B1 * | 10/2001 | Fitz | | 623/1.12 |
| 6,551,344 B2 * | 4/2003 | Thill | | 606/213 |
| 6,676,665 B2 * | 1/2004 | Foley et al. | | 606/105 |
| 6,755,868 B2 * | 6/2004 | Rousseau | | 623/23.64 |
| 6,913,607 B2 * | 7/2005 | Ainsworth et al. | | 606/151 |
| 6,969,397 B2 * | 11/2005 | Ginn | | 606/213 |
| 7,556,632 B2 * | 7/2009 | Zadno | | 606/142 |
| 7,662,168 B2 * | 2/2010 | McGuckin et al. | | 606/213 |
| 2002/0072768 A1 * | 6/2002 | Ginn | | 606/213 |
| 2002/0151921 A1 * | 10/2002 | Kanner et al. | | 606/190 |
| 2003/0009180 A1 * | 1/2003 | Hinchliffe et al. | | 606/144 |
| 2003/0045893 A1 * | 3/2003 | Ginn | | 606/151 |
| 2003/0093096 A1 * | 5/2003 | McGuckin et al. | | 606/157 |
| 2003/0158578 A1 * | 8/2003 | Pantages et al. | | 606/213 |
| 2006/0030867 A1 * | 2/2006 | Zadno | | 606/142 |
| 2006/0217744 A1 * | 9/2006 | Bender et al. | | 606/142 |
| 2007/0198058 A1 * | 8/2007 | Gelbart et al. | | 606/213 |
| 2007/0203507 A1 * | 8/2007 | McLaughlin et al. | | 606/144 |
| 2008/0065152 A1 * | 3/2008 | Carley | | 606/215 |
| 2008/0093414 A1 * | 4/2008 | Bender et al. | | 227/175.1 |
| 2009/0093826 A1 * | 4/2009 | Warder-Gabaldon | | 606/151 |
| 2009/0254121 A1 * | 10/2009 | Newth et al. | | 606/219 |
| 2010/0168790 A1 * | 7/2010 | Clark | | 606/213 |
| 2010/0217132 A1 * | 8/2010 | Ellingwood et al. | | |

* cited by examiner

*Primary Examiner* — Dianne Dornbusch
(74) *Attorney, Agent, or Firm* — Womble Carlyle Sandridge & Rice LLP

(57) ABSTRACT

A surgical tool may include a self-expanding combination anchor, comprising a first segment connected to a second segment, wherein said first segment is distal to said second segment.

14 Claims, 12 Drawing Sheets

US 9,138,212 B1

ANCHOR SYSTEM FOR PFO CLOSURE

This application claims priority to U.S. Provisional Patent Application Ser. No. 61/365,729, filed on Jul. 19, 2010, which is herein incorporated by reference in its entirety.

FIELD OF THE INVENTION

The present invention relates generally to a system for closing a patent foramen ovale in heart tissue.

BACKGROUND

Referring to FIG. 1, a patent foramen ovale (PFO) 2 is a flap-like opening in the wall 4 between the left atrium 6 and the right atrium 8 of the heart 10. That opening typically closes at or shortly after birth. However, in an estimated 20-25% of people, the PFO 2 remains open into adulthood. The PFO 2 allows blood clots in the bloodstream to bypass the natural filtering mechanism of the lungs, which can lead to stroke. A person with a PFO 2 is generally asymptomatic, and generally does not know he or she has a PFO 2 until after a stroke. In addition, research suggests a correlation between PFO 2 and migraine, the mechanism of which is still unknown.

Currently, patients having a known PFO 2 are treated in one of two ways. The patient may be prescribed blood thinners such as coumadin, to reduce the risk of clot formation. However, this course of treatment requires lifelong dependence on that medication, which does nothing to close the opening between the atria. Alternately, a device may be placed through the PFO 2 and then unfurled like a tent on each side of the PFO 2. Such a device may include a material such as polyester stretched over a wire frame, or stuffed inside a wire mesh. However, such devices can expose a significant amount of metal to the bloodstream, which is considered undesirable.

BRIEF DESCRIPTION OF THE DRAWINGS

The use of the same reference symbols in different figures indicates similar or identical items.

DETAILED DESCRIPTION

Commonly-assigned U.S. Patent Publication No. 2009/0093826 (Ser. No. 11/868,431) filed on Oct. 5, 2007 and published on Apr. 9, 2009 (the "PFO Document") is hereby incorporated by reference herein in its entirety.

Combination Anchor

Figure 1:
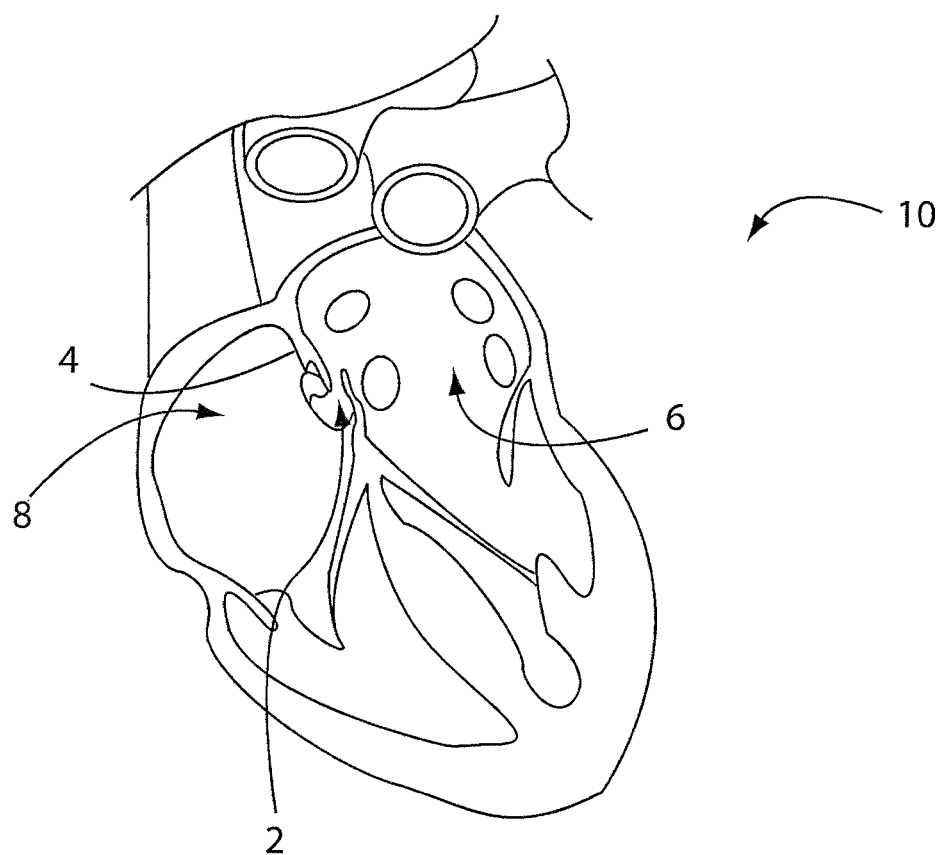
FIG. 1 is a cross-section view of a heart.
Figure 2:
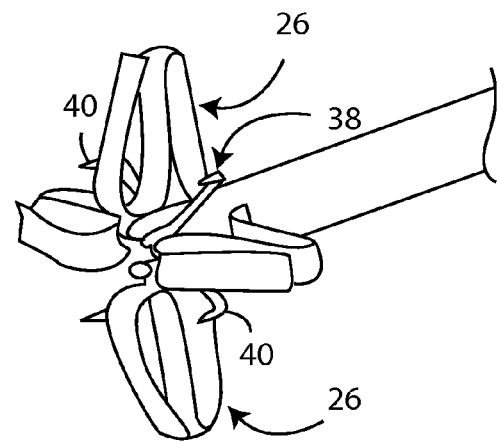
FIG. 2 is a perspective view of the distal end of a PFO closure tool.
Figure 3:
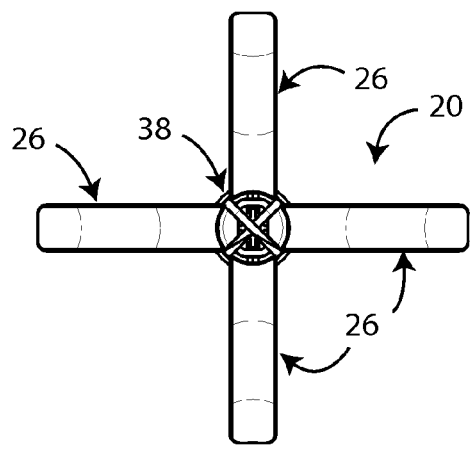
FIG. 3 is an end view of the distal end of a PFO closure tool.
Figure 4:
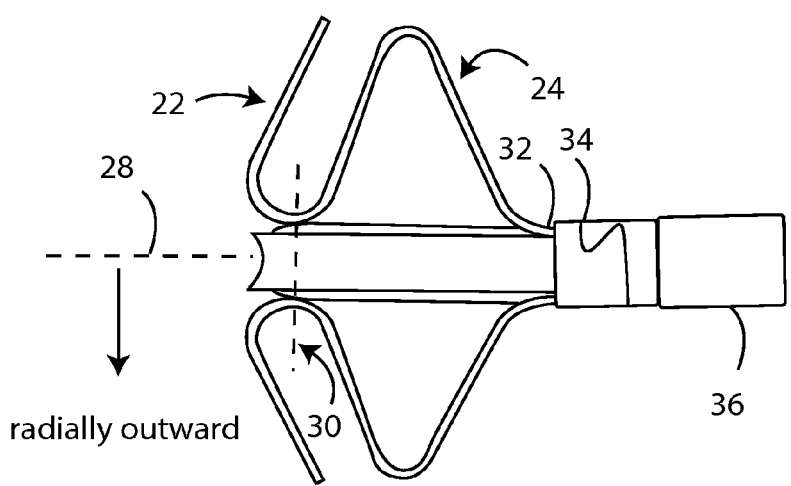
FIG. 4 is a side view of a combination anchor of the PFO closure tool of FIGS. 2-3 in a deployed state.

Referring also to FIGS. 2-4, a combination anchor 20 is shown in a deployed state. The combination anchor 20 is a unitary structure that includes a first segment 22 and a second segment 24. The first segment 22 is distal to and connected to the second segment 24. As described in greater detail below, the first segment 22 is configured for introduction into the left atrium 6 of the heart 10 and the second segment 24 is configured for introduction into the right atrium 8 of the heart 10. The combination anchor 20 also includes two or more fingers 26. The first segment 22 is defined as the distal segments of the fingers 26 collectively, and the second segment 24 is defined as the proximal segments of the fingers 26 collectively. The distal end of each finger 26 may be blunt. Referring to FIG. 4, in a deployed state, the free end of each finger 26 is located radially outward from the longitudinal centerline 28 of the combination anchor 20. The finger 26 may then extend inward toward the longitudinal centerline 28 of the combination anchor 20 and distal to the free end of the finger 26. Continuing to move along the finger 26 away from its free end, the finger 26 may curve such that an inflection point of the finger 26 is tangent to a line parallel to the longitudinal centerline 28 of the combination anchor 20. Substantially at that inflection point is the division 30 between the first segment 22 and the second segment 24. The finger 26 continues to curve outward, then extends proximally from and radially outward from the inflection point. The finger 26 may curve inward, then extend proximally and radially inward to a proximal end 32. The proximal end of the finger 26 may be fixed to a base 34 that may be generally cylindrical or that may have any other suitable shape. The base 34 in turn may be received within the lumen of a guide catheter 36 or other flexible tube. The base 34 may be the proximal end of the combination anchor 20.

The combination anchor 20 may include four fingers 26 arranged in an X-shape, where the fingers 26 are substantially evenly angularly arranged and radially symmetrically arranged about the longitudinal centerline 28 of the combination anchor 20, as seen in FIG. 3. However, more or less than four fingers 26 may be utilized. Further, the fingers 26 need not be evenly angularly arranged about the longitudinal centerline 28 of the combination anchor 20, nor radially symmetrically arranged about the longitudinal centerline of the combination anchor 20.

Advantageously, the combination anchor 20 is fabricated from nickel-titanium alloy. However, the combination anchor 20 may be constructed from any biocompatible superelastic alloy or material. Alternately, the combination anchor 20 may be fabricated from any material that is capable of self-expansion after removal of a constraining force.

A staple 38 may be held by the base 34. The staple 38, its retention by the base 34, and its deployment may be substantially as described in the PFO Document. The staple 38 may be substantially X-shaped as viewed on end. Advantageously, the tines 40 of the staple 38 are angularly spaced apart from the fingers 26 of the combination anchor 20 to prevent interference between the staple 38 and the combination anchor 20.

Figure 5:
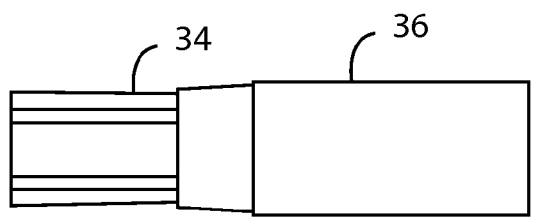
FIG. 5 is a side view of the combination anchor of the PFO closure tool of FIGS. 2-3 in an undeployed state.

The operation of the combination anchor 20 will now be described. Referring to FIG. 5, in an initial configuration, the base 34 is retracted far enough into the guide catheter 36 such that the guide catheter 36 constrains the fingers 26 of the combination anchor 20 radially, and such that the diameter of the base 34 and fingers 26 is substantially not greater than the diameter of the guide catheter 36. In this initial configuration, the base 34 may be partially or completely withdrawn into the lumen of the guide catheter 36.

As set forth in the PFO Document, the femoral artery, radial artery or other artery or vein in the vasculature remote from the PFO 2 may be punctured, and a standard introducer sheath may be placed into the puncture. A guidewire of the user's choosing may be inserted through the introducer sheath. Optionally, the guidewire may include a standard radiopaque feature at or near its distal end, to aid positioning of the distal end of the guide catheter 36 relative to the PFO 2. The guidewire may be advanced through the vasculature to the PFO 2, then completely through the PFO 2 into the left atrium 6. The guide catheter 36 then may be inserted through the introducer sheath over the guidewire and advanced through the vasculature to the PFO 2. The distal end of the guide catheter 36 then may be advanced completely through the PFO 2 into the left atrium 6. Alternately, the guide catheter 36 and the guidewire may be inserted substantially simultaneously, in which case the guidewire may be located completely within a lumen of the guide catheter 36, or may extend distally from the end of the guide catheter 36, during this advancement. Advancement of the guide catheter 36 and at least one guidewire advantageously may be performed with the assistance of a fluoroscope or other imaging device that indicates the position of the guide catheter 36 and/or at least one guidewire in the patient. The use of such an imaging device in conjunction with a guide catheter 36 and/or at least one guidewire is standard in the art. The guidewire may then be removed from the guide catheter 36. Alternately, the guide catheter 36 may be advanced to the PFO 2, then through the PFO 2 into the left atrium, without the use of a guidewire.

Figure 6:
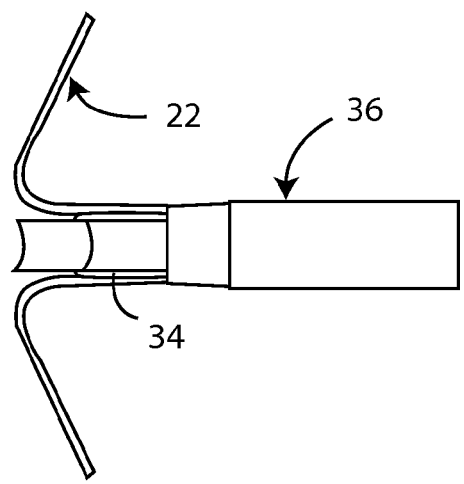
FIG. 6 is a side view of a first step in deployment of the combination anchor.
Figure 7:
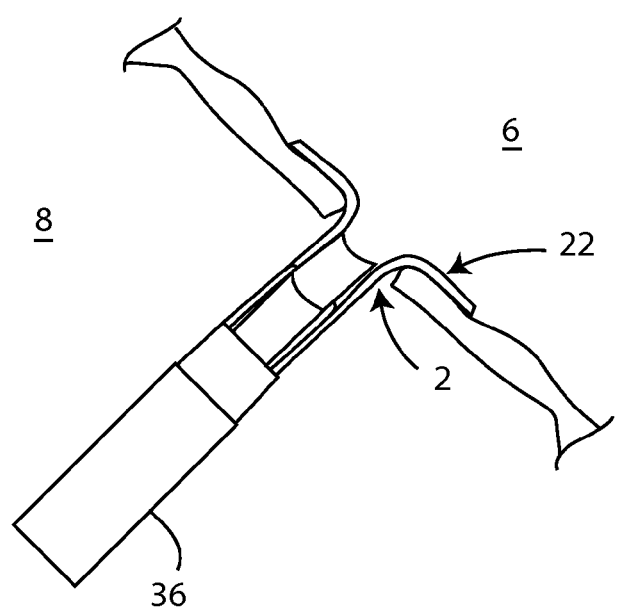
FIG. 7 is a side view of another step in deployment of the combination anchor.

Referring to FIG. 6, the base 34 then may be pushed distally relative to the end of the guide catheter 36. As the base 34 moves distally, the combination anchor 20 that is attached to the base 34 moves distally also. Continued motion of the base 34 causes the first segment 22 of the combination anchor 20 to move distal to the guide catheter 36, such that the guide catheter 36 no longer restrains the first segment 22. As a result, the distal ends of the fingers 26 self-expand radially outward to form the deployed first segment 22. Referring to FIG. 7, the guide catheter 36 and base 34 then may be retracted into the right atrium 8. Consequently, the first segment 22, which is positioned within the left atrium 6, is moved into contact with the wall of the left atrium 6 in proximity to the PFO 2. The expanded first segment 22 is too large to fit through the PFO 2 and thus holds the combination anchor 20 in place relative to the left atrium 6.

Figure 8:
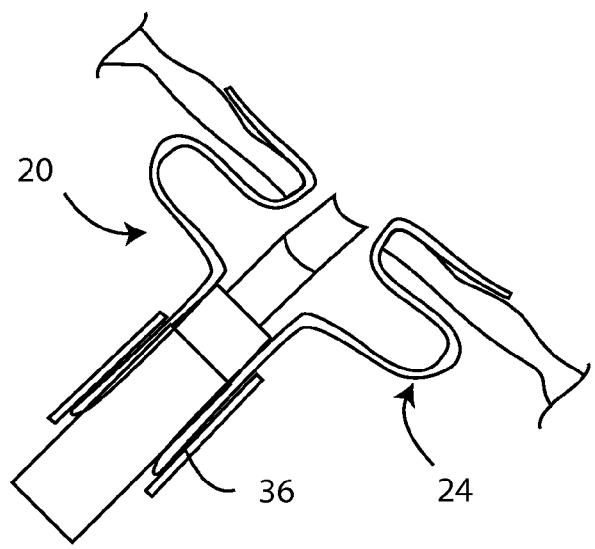
FIG. 8 is a side view of another step in deployment of the combination anchor.
Figure 9:
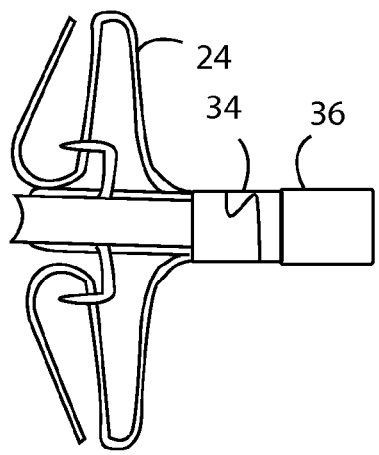
FIG. 9 is a side view of another step in deployment of the combination anchor.

Referring to FIG. 8, the guide catheter 36 may be withdrawn further distally. As a result, the proximal ends of the fingers 26 self-expand radially outward to form the deployed second segment 24. The deployed second segment 24 is located in the right atrium 8, on the opposite side of the PFO 2 from the first segment 22. Referring to FIG. 9, the base 34 may then be advanced distally relative to the guide catheter 36. As a result, the second segment 24 is compressed against the wall of the right atrium 8 relative to the first segment 22, thereby compressing tissue adjacent to the PFO 2 between the first segment 22 and the second segment 24 of the combination anchor 20. The second segment 24 may itself reduce in length longitudinally during this compression.

Figure 10:
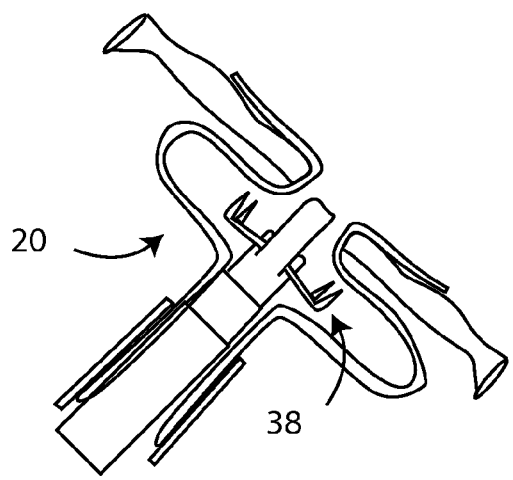
FIG. 10 is a side view of another step in deployment of the combination anchor.
Figure 11:
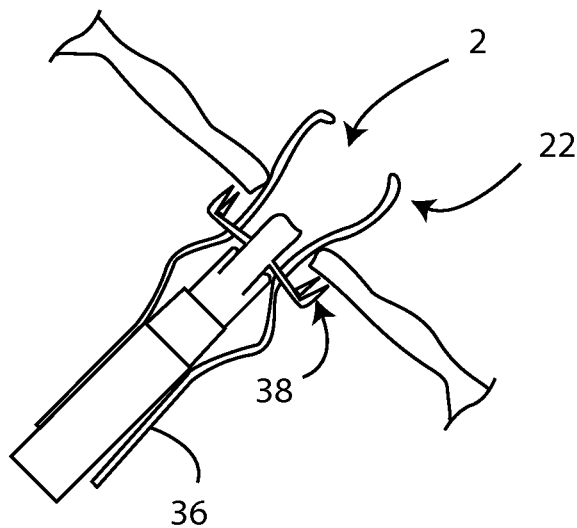
FIG. 11 is a side view of a step in the deployment of a staple.

Referring also to FIG. 10, the tines 40 of the staple 38 then may be splayed, as set forth in the PFO Document. The base 34 then may be advanced, driving the tips of the tines 40 into tissue adjacent to the PFO 2. The staple 38 may then be separated from the base 34. Alternately, the tines 40 need not be driven into tissue at all at this time. Alternately, the staple 38 may be completely deployed into heart tissue adjacent to the PFO 2 at this time. Referring to FIG. 11, the base 34 then may be retracted proximally and/or the guide catheter 36 may be advanced distally, causing the second segment 24 to compress within the lumen of the guide catheter 36. Further proximal motion of the base 34 and/or distal motion of the guide catheter 36 causes the first segment 22 to compress back into the lumen of the guide catheter 36 as well.

Figure 12:
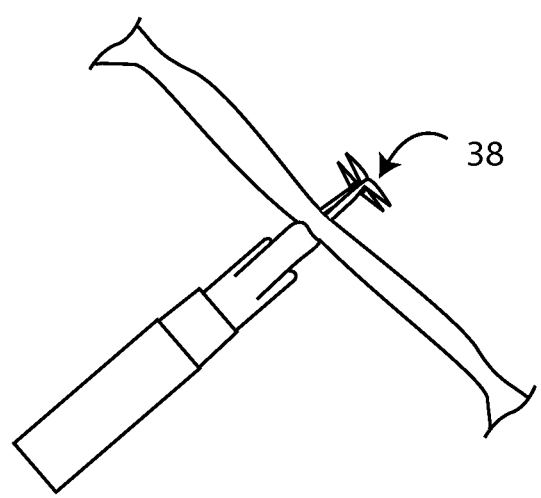
FIG. 12 is a side view of another step in the deployment of a staple.
Figure 13:
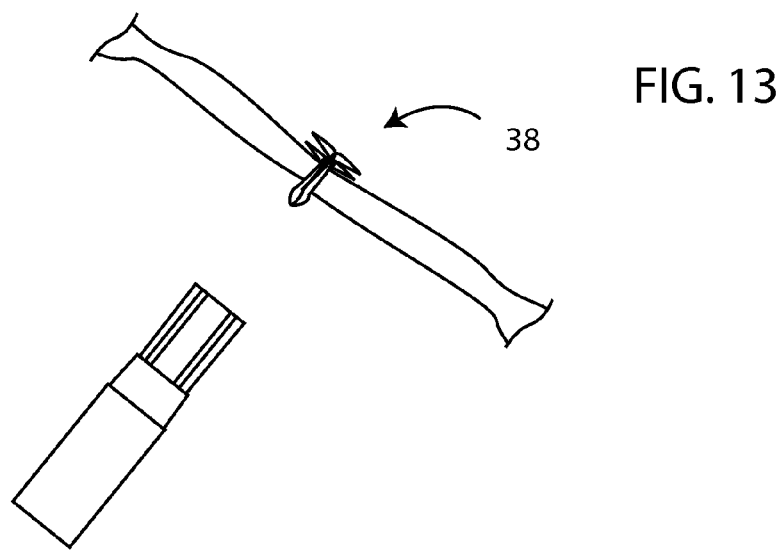
FIG. 13 is a side view of a completed staple deployment.

Referring also to FIG. 12, the staple 38 is then closed to close the PFO 2. Closure of the staple 38 may be as set forth in the PFO Document, or may be performed in any other suitable manner. Referring to FIG. 13, the guide catheter 36 is then withdrawn from the heart 10 and from the insertion point into the patient, which itself is then closed in any suitable manner. The PFO 2 is closed and the procedure is complete.

One-Sided Anchor

Figure 14:
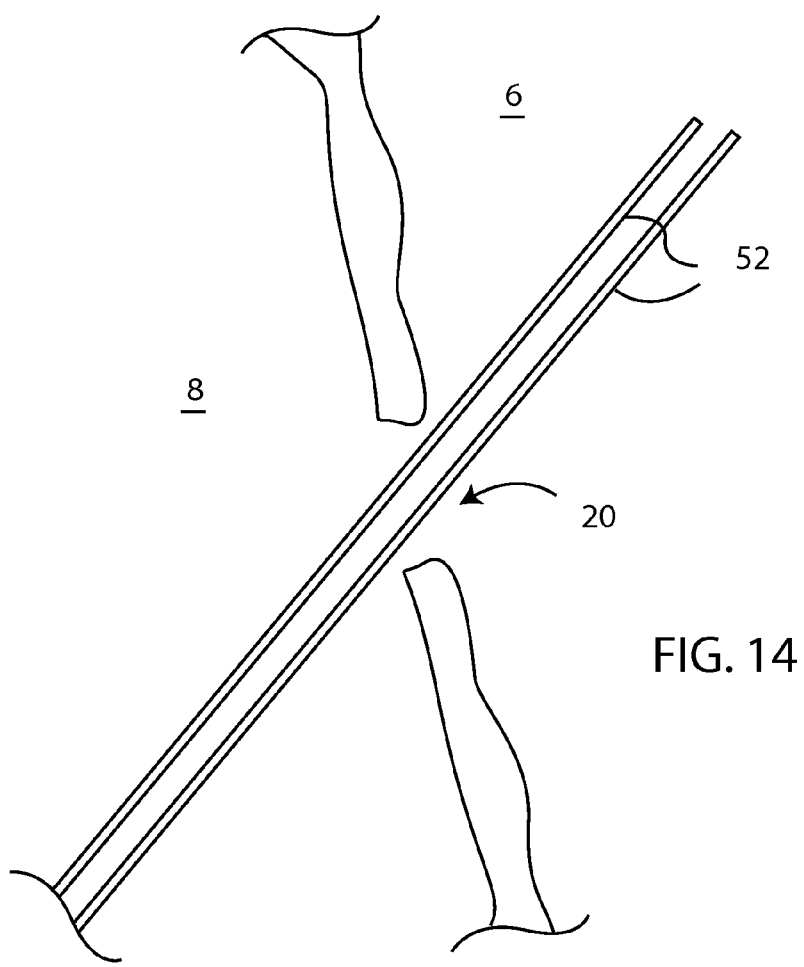
FIG. 14 is a side view of a first step in deployment of another embodiment of an anchor.
Figure 15:
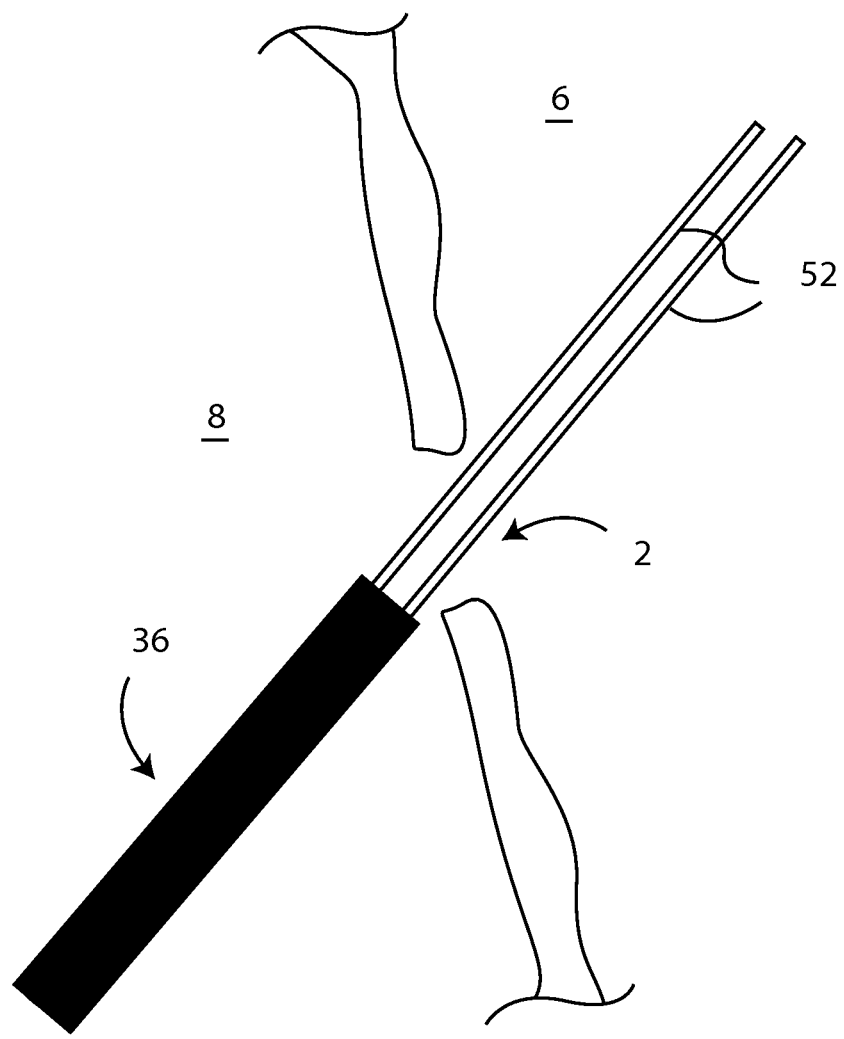
FIG. 15 is a side view of another step in deployment of the anchor of FIG. 15.

As another example of an anchor 50, the anchor 50 may be one-sided such that it expands only on a single side of the PFO 2. Referring to FIG. 14, one or more guidewires 52 are inserted through the patient's vasculature as set forth above, through the PFO 2 and into the left atrium 6. Referring to FIG. 15, the guide catheter 36 may be advanced over the guidewires 52 into the right atrium 8.

Figure 16:
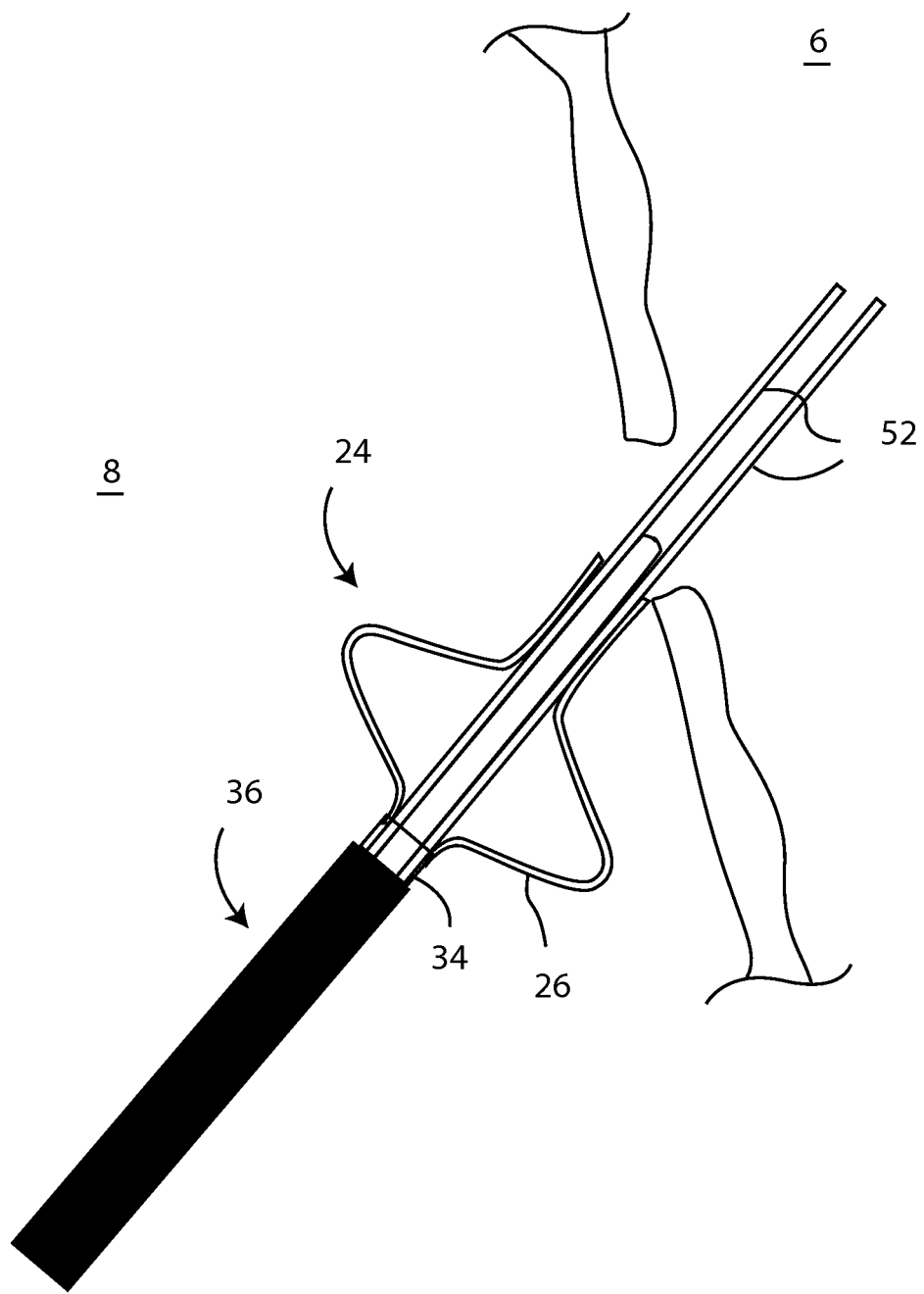
FIG. 16 is a side view of another step in deployment of the anchor of FIG. 15.

Referring also to FIG. 16, the guide catheter 36 then may be withdrawn proximally. As set forth above, a base 34 may be provided, with fingers 26 attached thereto that form a second segment 24. Withdrawal of the guide catheter 36 allows the second segment 24 to self-deform radially outward. The first segment 22 set forth above may be omitted, such that the anchor 50 only includes a second segment 24 configured to deploy in the right atrium 8; in other respects, the anchor 50 may be substantially as set forth above with regard to the combination anchor 20. The term "second segment 24" is used for convenience in description here, to be consistent with the description of the combination anchor 20 above, even though the anchor 50 only includes a single segment.

Figure 17:
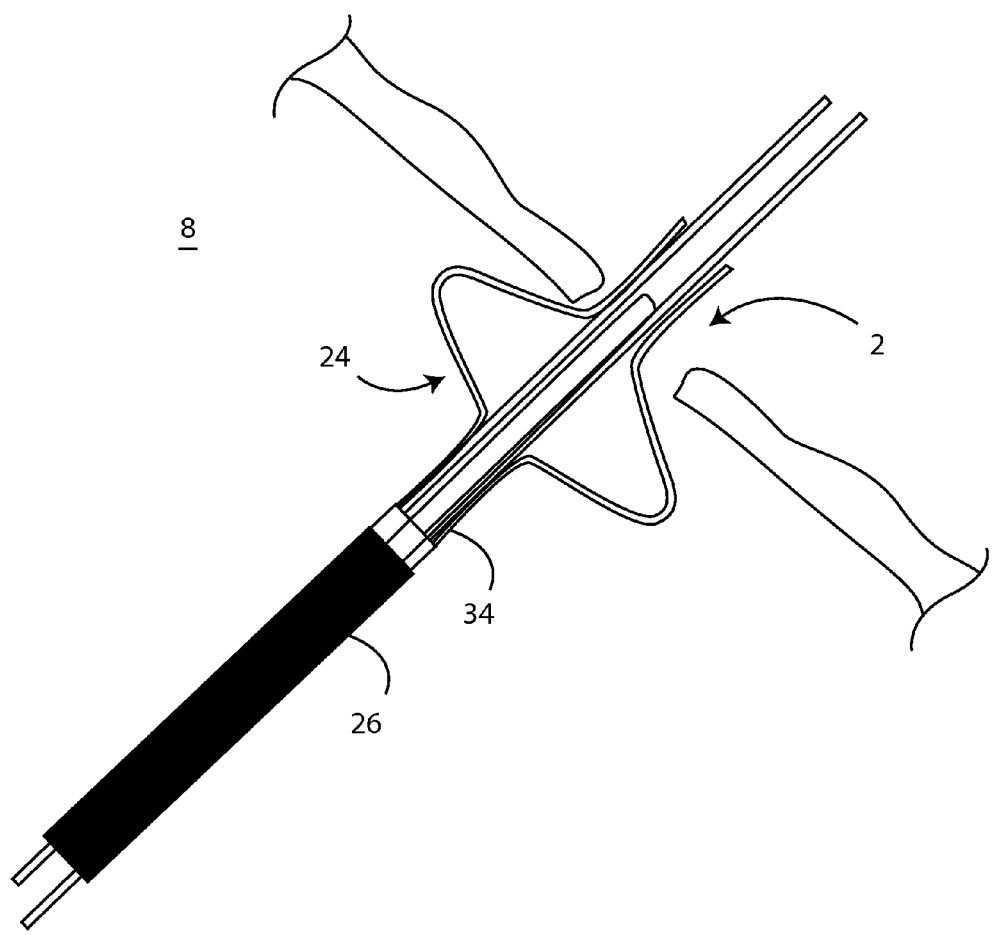
FIG. 17 is a side view of another step in deployment of the anchor of FIG. 15.
Figure 18:
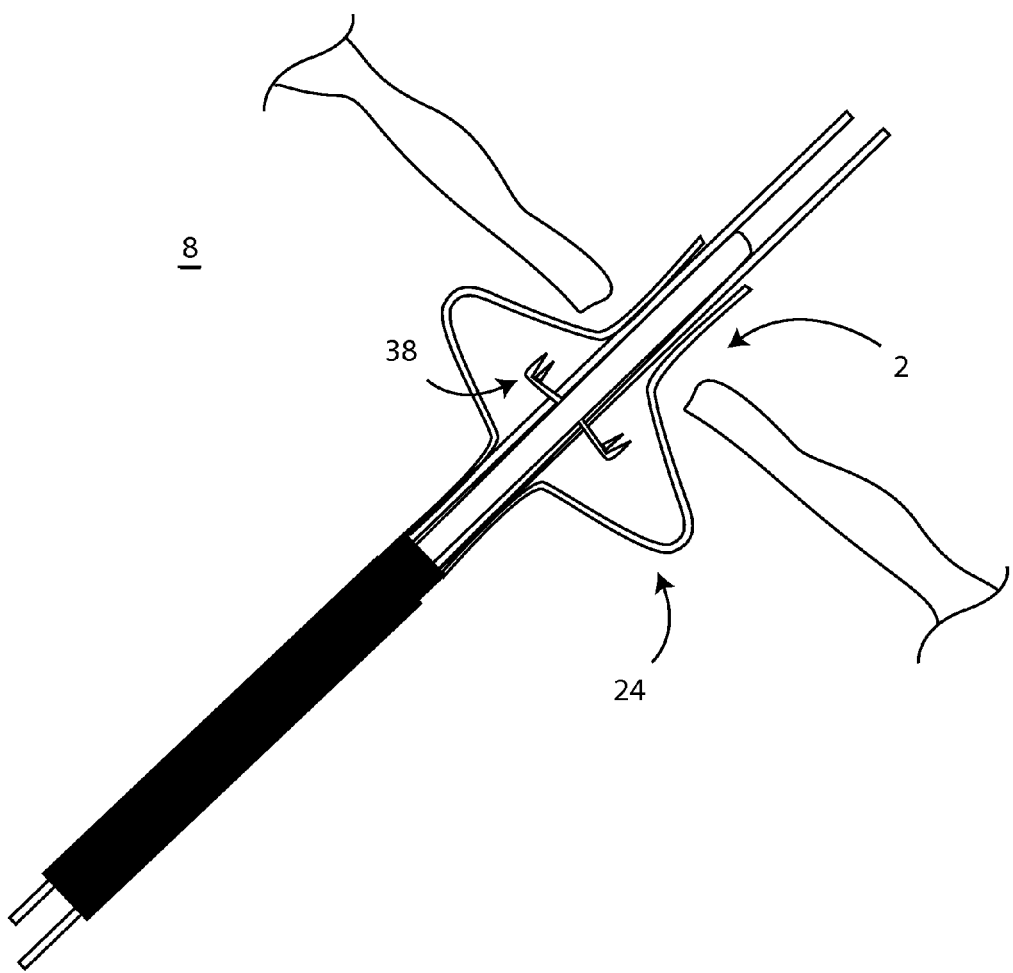
FIG. 18 is a side view of another step in deployment of the anchor of FIG. 15.
Figure 19:
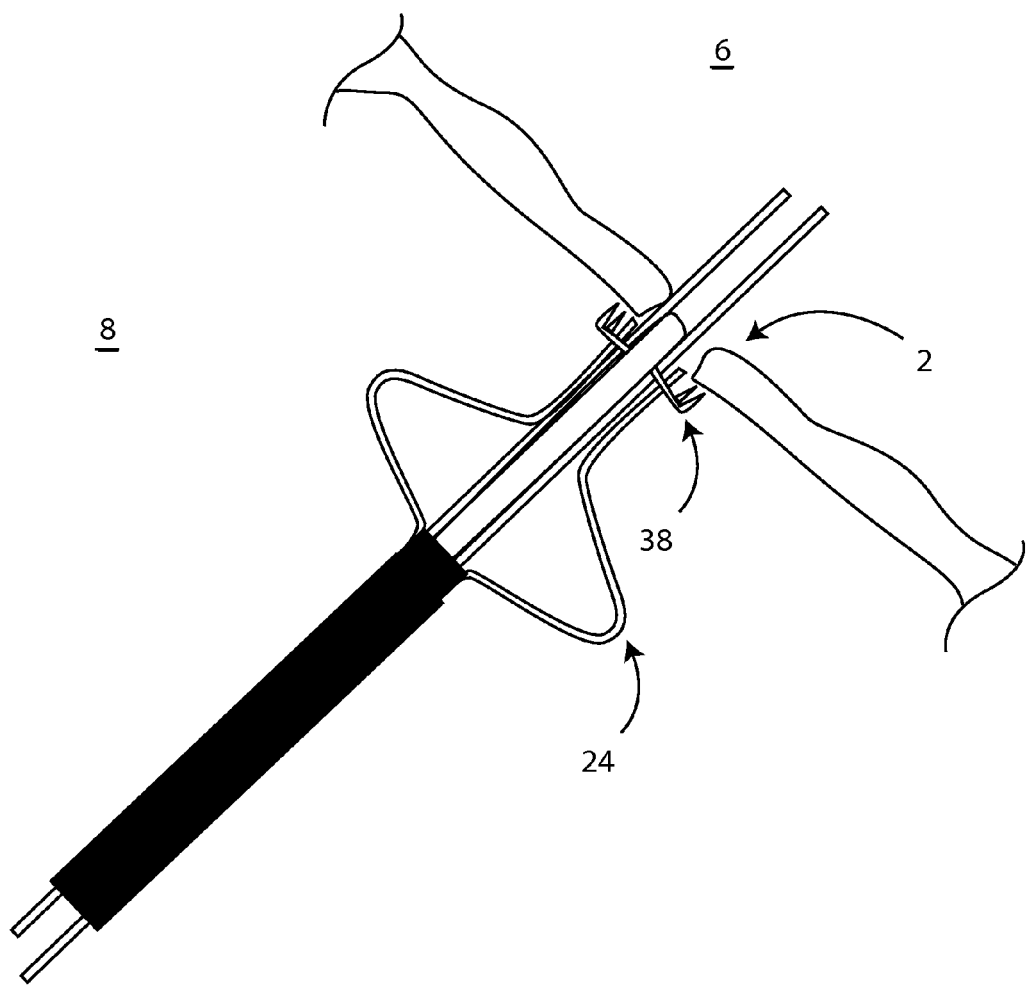
FIG. 19 is a side view of another step in deployment of the anchor of FIG. 15.
Figure 20:
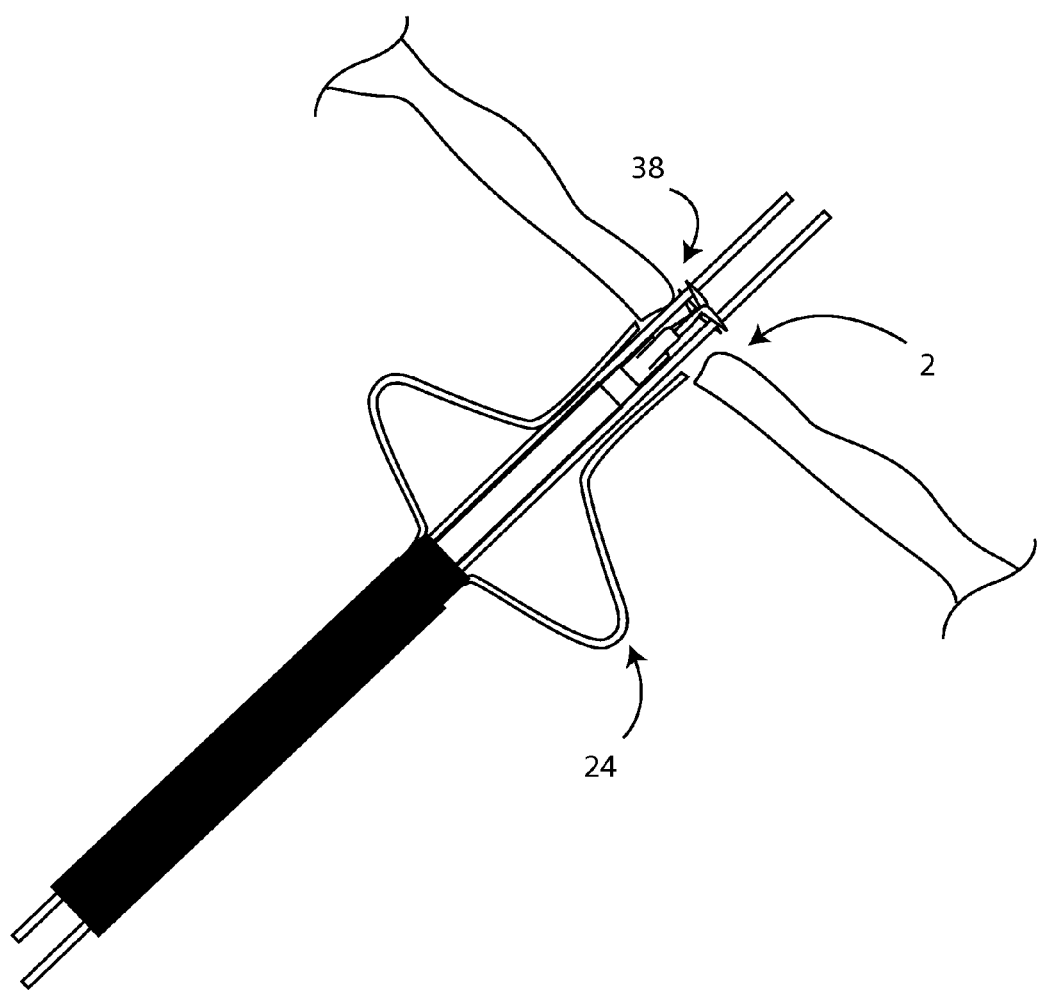
FIG. 20 is a side view of a completed staple deployment.

Referring also to FIG. 17, the guide catheter 36 and base 34 are advanced distally to place the second segment 24 against tissue of the right atrium 8 adjacent to the PFO 2. The second segment 24 is pushed against the tissue of the right atrium 8 to tension it and provide a suitable surface for staple deployment. Referring also to FIG. 18, the staple 38 is splayed, as set forth in the PFO Document. Referring also to FIG. 19, the staple 38 is advanced into tissue adjacent to the PFO 2. The second segment 24 is then retracted proximally away from the PFO 2, into the right atrium 8. Referring also to FIG. 20, the staple 38 is then closed to close the PFO 2. Closure of the staple 38 may be as set forth in the PFO Document, or may be performed in any other suitable manner. The guide catheter 36 and guidewires 52 are then withdrawn from the heart 10 and from the insertion point into the patient, which itself is then closed in any suitable manner. The PFO 2 is closed and the procedure is complete.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical tool, comprising:
   a self-expanding combination anchor, comprising two or more fingers, each finger comprising a distal end and a proximal end, and a first segment connected to a second segment, wherein said first segment of each finger is distal to said second segment of said each finger, and
   a base having the proximal end of each of the two or more fingers coupled to the base, wherein the base is moveable from a first position to a second position, the first position constraining the two or more fingers of the self expanding combination anchor in a substantially straight configuration and the second position enabling expansion of the two or more fingers of the self expanding combination anchor, wherein the expansion of the two or more fingers defines opposing U-shaped openings having open ends oriented outward from the base and closed ends that respectively contact surfaces of a guide catheter along lines that are parallel to a longitudinal center of the combination anchor.

2. The surgical tool of claim 1, wherein a free end of the distal end of each finger is oriented radially outward from a longitudinal axis of the anchor.

3. The surgical tool of claim 1, wherein each finger further comprises a first curved portion located radially inward from the distal end of said each finger.

4. The surgical tool of claim 3, wherein the first curved portion of each finger has an inflection point substantially tangent to a line substantially parallel to a longitudinal axis of the anchor.

5. The surgical tool of claim 3, wherein the first curved portion of each finger includes a portion of the first segment and a portion of the second segment of said each finger.

6. The surgical tool of claim 3, wherein each finger further comprises a second curved portion, the second curved portion oriented radially outward from the first curved portion of said each finger.

7. The surgical tool of claim 6, wherein the second curved portion of each finger is a portion of the second segment of said each finger.

8. The surgical tool of claim 6, wherein each finger curves radially inward proximal to the second curved portion of said each finger.

9. The surgical tool of claim 1, wherein the anchor comprises four fingers.

10. The surgical tool of claim 1, wherein the anchor forms an X-shape.

11. The surgical tool of claim 1, wherein the base is operable to drive a staple supported by the base when the base is in the second position.

12. The surgical tool of claim 1, wherein the each of the opposing U-shaped openings have an opening extending radially outward from a longitudinal axis of the anchor.

13. The surgical tool of claim 12, further comprising a staple that is X-shaped.

14. The surgical tool of claim 13, wherein tines of the staple are angularly spaced apart from the fingers.

* * * * *